United States Patent [19]

Shimizu et al.

[11] Patent Number: 4,985,456

[45] Date of Patent: Jan. 15, 1991

[54] 2-ANILINOPHENYLACETIC ACID DERIVATIVE

[75] Inventors: Keisuke Shimizu, Mie; Takumi Matsumura; Masato Nakamoto, both of Toyama, all of Japan

[73] Assignees: Mikasa Seiyaku Co., Ltd., Tokyo; Daito Koeki Kabushiki Kaisha, Toyoma, both of Japan

[21] Appl. No.: 478,025

[22] Filed: Feb. 9, 1990

Related U.S. Application Data

[63] Continuation of Ser. No. 152,810, Feb. 5, 1988, abandoned.

[51] Int. Cl.$^5$ .................. A61K 31/335; C07D 317/24
[52] U.S. Cl. ...................................... 514/467; 549/229; 549/230
[58] Field of Search ................ 549/229, 230; 514/467

[56] References Cited

U.S. PATENT DOCUMENTS

| | | | |
|---|---|---|---|
| 3,558,690 | 1/1971 | Sallmann et al. | 564/211 |
| 4,536,515 | 8/1985 | Belanger et al. | 549/230 |
| 4,654,331 | 3/1987 | Christensen | 549/229 |

FOREIGN PATENT DOCUMENTS

| | | | |
|---|---|---|---|
| 0237084 | 9/1987 | European Pat. Off. | 549/229 |

Primary Examiner—Glennon H. Hollrah
Assistant Examiner—Susan P. Treanor
Attorney, Agent, or Firm—Birch, Stewart, Kolasch & Birch

[57] ABSTRACT

(5-methyl-2-oxo-1,3-dioxolen-4-yl)methyl 2-(2,6-dichloroanilino)phenylacetate is disclosed as a novel compound possessing strong valuable pharmacological properties accompanied by surprisingly weak side-effects as well as a process for preparing the new compound.

2 Claims, No Drawings

2-ANILINOPHENYLACETIC ACID DERIVATIVE

This application is a continuation of application Ser. No. 07/152,810 filed on Feb. 5, 1988, now abandoned.

BACKGROUND OF THE INVENTION

1. Field of the Invention

The present invention relates to a novel 2-anilinophenylacetic acid derivative possessing durable and strong valuable pharmacological effects with less side-effects and to a process for preparing the same. More particularly, the present invention relates to (5-methyl-2-oxo-1,3-dioxolen-4-yl)methyl 2-(2,6-dichloroanilino)-phenylacetate possessing durable and strong valuable pharmacological properties accompanied by an extremely low level of side-effects and to a process for preparing the same.

2. Description of the Prior Art

From the past, a great number of non-steroid drugs have been developed as possessing anti-inflammatory, antipyretic, analgesic and/or anti-rheumatic activity. The drugs developed hitherto are generally classified into several groups; drugs of the salicylic acid series such as various aspirin preparations including bufferin, those of the anthranilic acid series such as mefenamic acid and flufenamic acid, those of the phenylacetic acid series such as alclofanac, diclofenac and fenbufen, those of the indole series such as indomethacin, those of the indene series such as sulindac, those of the heteroarylacetic acid series such as tolmecin, those of the propionic acid series such as ibuprofen, naproxen, ketoprofen and flurbiprofen, those of the prazolone series such as phenylbutazone, oxyphenbutazone, azapropazone, clofezone, ketophenylbutazone and succibutazone, those of the benzothiazine series such as piroxicam, those of the phenothiazine series such as metiazinic acid, those of the pyrimidine series such as bucolome, those of the indazole series such as benzydamine, those of pyrimidinylpyrazole series such as mepirizol, those of the thienopyridine series such as tinoridine hydrochloride, and those of the benzothiazolinone series such as tiaramid hydrochloride. However, these drugs are weak in their main pharmacological activities or concurrently exhibit relatively high toxicity in comparison with their main pharmacological activities so that a consecutive administration of the drugs over a long period of time will result in the occurrence of serious side-effects or drug-tolerance.

In the case of drugs of the salicylic acid series such as aspirin preparations, for example, the use in a smaller dose exhibits strong anti-inflammatory, antipyretic and analgesic activities while the use in a larger dose displays anti-rheumatic activity. On the other hand, however, the consecutive use of these drugs induces tinnitus and seriously attacks digestive organs and liver, especially the stomach. The use of drugs of the anthranilic acid series such as mefenamic acid exhibit analgesic activity but with poor anti-inflammatory activity and induces, on the other hand, lesion, diarrhoea and digestive system disorder. The use of drugs of the phenylacetic acid series possess relatively weak side-effects but exhibit only a medium degree of anti-inflammatory, antipyretic and analgesic activities. The use of drugs of the indole series such as indomethacin exhibits especially remarkable anti-rheumatic activity in addition to anti-inflammatory and analgesic activities but influences the central nervous system so as to cause headaches and giddiness and induces various side-effects including digestive system disorders. In the case of drugs of the indene series such as sulindac, the side-effects on the central nervous system as seen in the drugs of the indole series are almost eliminated but a medium degree of digestive system disorder still remains as side-effects. The use of drugs of the heteroarylacetic acid series exhibits strong analgesic activity but with digestive system disorders. The use of drugs of the propionic acid series such as ibuprofen is now recommended because of their weak side-effects. On the other hand, however, these drugs are not so strong in their main pharmacological effects although they possess anti-inflammatory, antipyretic and analgesic activities on the average. Drugs of the pyrazolone series such as phenylbutazone exhibit various pharmacological effects in addition to anti-inflammatory and analgesic activities but permit the occurrence of various side-effects including lesions, edema, blood dyscrasia, hepatic disorders and digestive system disorders. Drugs of the benzothiazine series exhibit rapid and durable anti-inflammatory, antipyretic and analgesic activities of medium degree but concurrently exhibit edema and digestive system disorders.

Thus, all of the drugs now commercially available as exhibiting anti-inflammatory, antipyretic and analgesic activities produce more or less side-effects. If such side-effects are substantially eliminated, the main pharmacological effects are in toto enhanced and the consecutive use of such drugs becomes possible to exhibit strong pharmacological activities. Accordingly, there is still great demand for developing a new compound which exhibits strong pharmacological activities with negligibly weak side-effects.

BRIEF SUMMARY OF THE INVENTION

Accordingly, it is an object of the present invention to provide a new 2-anilinophenylacetic acid derivative possessing durable and strong valuable pharmacological activities with negligible side-effects.

It is another object of the present invention to provide a novel non-steroid anti-inflammatory and analgesic drug accompanied with a negligibly low level of toxicity and side-effects.

It is still another object of the present invention to provide a process for preparing such novel compound.

Other objects, features and advantages of the present invention will become apparent more fully from the following detailed description.

With a view to developing a new type anti-inflammatory drug which is strong and durable in pharmacological effects with negligible side-effects, the present inventors have synthesized a series of new arylacetic acid derivatives and analyzed their pharmacological activities. As a result of such extensive research, it has now been found that a new compound of the 2-anilinophenylacetic acid series having the formula:

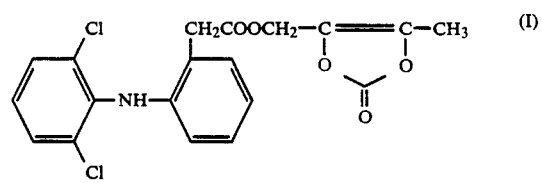

possesses extremely strong and remarkable anti-inflammatory and analgesic activities with negligible side-effects represented by digestive system disorders. The present invention has been accomplished on the basis of the above finding.

In accordance with one and the prime embodiment of this invention, there is provided (5-methyl-2-oxo-1,3-dioxolen-4-yl)methyl 2-(2,6-dichloroanilino)phenylacetate of the formula:

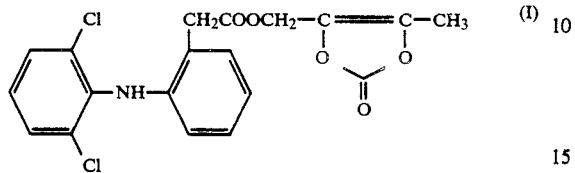

In accordance with another embodiment of this invention, there is provided a process for the preparation of (5-methyl-2-oxo-1,3-dioxolen-4-yl)methyl 2-(2,6-dichloroanilino)phenylacetate of the formula:

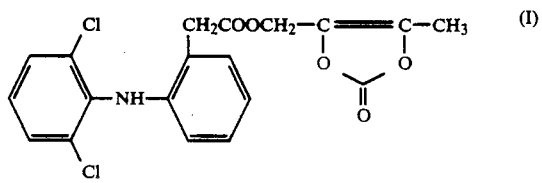

which comprises reacting a salt of 2-(2,6-dichloroanilino)-phenylacetic acid of the formula:

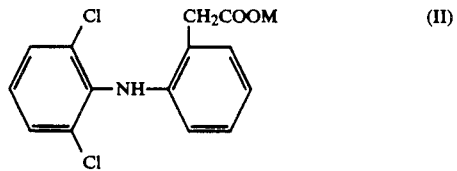

wherein M is an alkali metal or ammonium group of an organic tertiary amine, with a 4-methyl-5-halogenomethyl-1,3-dioxolen-2-one of the formula:

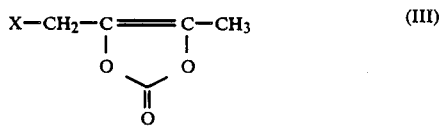

wherein X is a halogen atom.

DETAILED DESCRIPTION OF THE INVENTION

The new compound of this invention is a white crystalline substance soluble in organic solvents such as alcohols and can be prepared by reacting the compound of the formula (II) with the compound of the formula (III) in a manner known per se for condensation.

The compound of the formula (II) and the compound of the formula (III) are both known compounds. The compound of the formula (II) is prepared, for example, according to the methods as described in Japanese Patent Publn. No. Sho. 42-23418 by saponification of the corresponding ester, acidic hydrolysis of the corresponding nitrile or alkaline hydrolysis of a lactam of the formula:

The corresponding nitrile is prepared by reacting an α-halogeno-N-phenyl-o-toluidine such as α-chloro-N-(2,6-dichlorophenyl)-o-toluidine with an alkali metal cyanide such as KCN. The compound of the formula (IV) is prepared according to several methods, for example, by heating 2-chloro-N-(2,6-dichloro)-phenylacetanilide with aluminum chloride at about 160° C. or at 100°–150° C. in tetrachloroethane or nitrobenzene.

The compound of the formula (III) is prepared, for example, according to a method as described in Japanese Laid-open Patent Appln. No. Sho. 57-26684 by reacting 4,5-dimethyl-1,3-dioxolen-2-one with a chlorinating agent such as gaseous chlorine, N-chlorosuccinimide or N-chlorophthalimide under a radical-generating condition (irradiation of UV-rays or the use of a radical-generating agent such as a peroxide) at room temperature or an elevated temperature.

The new compound of this invention represented by the formula (I) can be prepared by reacting the compound of the formula (II) with the compound of the formula (III) according to a condensation reaction. From another viewpoint, this condensation reaction can be regarded as one mode of the esterification reaction wherein a functionally reactive carboxylic acid is reacted with a hydroxy compound the hydroxyl group of which has been converted into a functionally reactive form. Thus, the reaction between the compound of the formula (II) and the compound of the formula (III) is carried out in the presence of an organic solvent optionally with a base as an acid-binding agent.

Any of the organic solvents can be used for the above reaction so far as the solvent does not influence the reaction. In general, ketones, ethers, nitriles and esters can conveniently be used as the solvent, but alkyl halides or the like reactive solvents are not recommended as the solvent. Illustrative of the preferable solvent are, for example, acetone, methyl ethyl ketone, tetrahydrofuran, dioxane, dimethylformamide, diethylformamide, triethylamine and pyridine.

The use of the base as an acid-binding agent is not indispensable for the above reaction but is preferable for the reason that the reaction is promoted in the presence of a base. In the present invention, the utilizable base is not extremely strong but mild in alkalinity. Illustrative of the base as acid-binding agent are, for example, sodium carbonate, potassium carbonate, sodium hydrogen carbonate, potassium hydrogen carbonate, triethylamine, pyridine and picoline. The use of an organic weak base such as sodium or potassium hydrogen carbonate is preferable. These bases are generally used in a smaller amount as compared with the reactants, but triethylamine may be used in a larger amount as its excess portion serves as the reaction solvent.

No particular limitation exists in the proportion of the reactants. In general, however, the reactants are used in stoichiometric amount. The reaction solvent is used at least in an amount sufficient to form a solution or suspension of the reactants.

The reaction is carried out at a temperature ranging from −10° C. to the boiling point of the solvent used. The reaction temperature is preferably selected from the range from 10° C. to 80° C. The reaction time varies according to the condition employed but is generally within the period of 1–3 hours.

The new 2-anilinophenylacetic ester thus obtained is separated from the reaction mixture and purified by recrystallization from an alcohol.

As a result of various tests made on the pharmacological activities of the new compound of this invention, it has been found that the new compound is comparable in anti-inflammatory activity with the known compounds which are now regarded as being strongest in anti-inflammatory activity, but is extremely weak in side-effects represented by gastric ulcerogenic action as compared with the known compounds. Thus, the compound of this invention is in too much stronger in anti-inflammatory and analgesic activities than the known compounds. This fact is evident from the following tests on the pharmacological effects:

1. Tests of the pharmacological effects (a) Inhibitory effect on carrageenin-induced hind paw edema in rats:

40 Male rats of Wistar strain weighing 100–130 g were divided into the following 5 groups each consisting of 8 rats: 1. Control group, 2. Group for the administration of the compound of this invention, 3. Group for the administration of diclofenac Na, 4. Group for the administration of flurubiprofen and 5. Group for the administration of indomethacin. Prior to the administration of the test compounds, plantar injection of a 1% carrageenin solution was made to each rat to induce hind paw edema. To each rat of the Groups 3, 4 and 5, the $ED_{50}$ amount of the relevant test compound was orally administered in terms of a molar amount. The compound of the present invention was administered in an equimolar amount to diclofenac sodium salt.

As a result of comparison in inhibitory effects of the test compounds on hind paw edema induced by carrageenin, swelling of the edema was significantly inhibited in all of the Groups to which the test compounds were administered as compared with the Control group ($P<0.01$). However, no significant difference in inhibitory effect was observed between Group 2 to which the compound of this invention was administered and all other Groups to which the other test compounds were administered. It has been manifested therefore that the compound of this invention is comparable in inhibitory effects on carrageenin-induced hind paw edema in rat with diclofenac sodium salt, indomethacin and flurubiprofen which are known to be strong anti-inflammatory drugs.

(b) Analgesic and anti-capillary permeability effects according to Wittle's method:

Three groups of female mice of ICR strain weighing 22–28 g were used, each group consisting of 10 mice; one group (Group 1) being provided for the administration of the compound of this invention, another group (Group 2) for the administration of diclofenac sodium salt and the other group (Group 3) for control. Each test compound was orally administered in a dose of 25 mg/kg to mice of the relevant group, and 20 minutes after the oral administration, a 4% Pontamine Sky Blue (PSB) solution was intravenously injected to each mouse of Groups 1, 2 and 3, and 10 minutes after the injection, 1% acetic acid was intraperitoneally injected to each mouse. Immediately after the intraperitoneal injection, the number of stretchings of the treated mice were counted and recorded for 20 minutes. After this observation, the mice were immediately sacrificed by dislocation of cervical vertebrae and subjected to ventrotomy. The peritoneal cavity of each mouse was washed with 5 ml of distilled water to exudate PSB in the peritoneal cavity, and the amount of the colorant exudated was measured.

As a result of the tests, it was manifested that Groups 1 and 2 showed significant differences in inhibitory activities to stretching and exudation of the colorant in peritoneal cavity from Group 3 ($P<0.01$). No significant difference in analgesic and anti-capillary permeability effects was found between Groups 1 and 2. Thus, the compound of this invention is comparable in these effects with diclofenac sodium salt.

2. Acute toxicity and gastric ulcerogenic actions (a) Acute oral toxicity in mice:

Groups of male and female mice of ICR strain weighing 25–35 g were used for the test, each group consisting of 6 mice. The compound of this invention was orally administered in a dose of 250 mg/kg, 290 mg/kg, 336 mg/kg, 390 mg/kg or 452 mg/kg to the mice of each group. $LD_{50}$ values of the compound of this invention were calculated for each concentration according to the Litchfield-Wilcoxon's method from the number of dead mice during one week. The $LD_{50}$ values for oral administration of the compound of this invention was determined as 460 mg/kg for male mice and 516 mg/kg for female mice. These values were approximately 3 times as high as those of diclofenac sodium salt showing 145 mg/kg for male mice and 135 mg/kg for female mice.

(b) Gastric ulcerogenic action:

Three groups of male rats of Wistar strain weighing 300–340 g were used, each group consisting of 7 rats; one group (Group 1) being provided for control, another group (Group 2) for the administration of the compound of this invention and the other group (Group 3) for the administration of diclofenac sodium salt. After 24 hour fasting prior to the test, the compound of this invention and diclofenac sodium salt were orally administered each in a dose of 20 mg/kg to the rats of the relevant groups. Six hours after the administration, the rats were sacrificed by decaptation and their stomachs were immediately removed. A 5% formaline (10 ml) was injected through cardia into the stomach cavity and the stomach was fixed overnight in a 10% formaline. Each fixed stomach was incisioned along the greater curvature, and the inside of the stomach was investigated with naked eyes to check whether ulcer and erosion occurred or not. An ulcerogenic and erosion index was $0.71\pm0.42$ in Group 1, $1.13\pm0.40$ in Group 2 and $17.57\pm4.28$ in Group 3. The number of rats having ulcer or erosion was 3/7 (42.9%) in Group 1, 4/7 (57.1%) in Group 2 and 7/7 (100%) in Group 3.

No significant difference was found between Group 1 and Group 2 with respect to the number of rats having ulcer or erosion. However, significant differences were found between Group 3 and Groups 1 and 2 in the ulcerogenic and erosion index and the number of rats having ulcer or erosion ($P<0.01$).

The above fact apparently shows that the gastric ulcerogenic action of the compound of this invention as side-effects is extremely weak and almost negligible as compared with that of diclofenac sodium salt which is one of the known strong anit-inflammatory drugs. It is evident therefore that the compound of this invention is in toto stronger in anti-inflammatory and analgesic activities than any of the known strong similar drugs.

The present invention will now be illustrated in more detail by way of an example.

EXAMPLE 6.5 Grams (20 m-mol) of sodium 2-(2,6-dichloroanilino)-phenylacetate was dispersed in 45 ml of dimethylformamide, and 0.4 g (4 m-mol) of potassium hydrogen carbonate was added to the dispersion. To this dispersion under ice cooling was then added dropwise 4.3 g (22 m-mol) of 4-bromomethyl-5-methyl-1,3-dioxolen-2-one. The mixture was stirred for one hour at room temperature and then for one hour at 60° C. After completion of the reaction, the reaction liquid was cooled down to room temperature and then dispersed in ice water. The oily substance separated was extracted with benzene, and the extract was washed with water, dried and then concentrated by distilling off the solvents. The residual substance obtained was recrystallized from methanol whereby 6.9 g (yield: 85%) of (5-methyl-2-oxo-1,3-dioxolen-4-yl)methyl 2-(2,6-dichloroanilino)phenylacetate was obtained as white crystals.

Melting point: 92° C.

Analysis ($C_{19}H_{15}Cl_2NO_5$): Calcd. (%) C,56.16; H,3.71; N,3.47. Found. (%) C,55.90; H,3.70; N,3.43.

IR (KBr, $\nu cm^{-1}$): 3320 (NH); 1820 (ringed carbonyl ester); 1735, 1715 (ester).

NMR (CDCl$_3$, δppm): 2.15 (3H,s,methyl) 3.85 (2H,s,—CH$_2$CO)

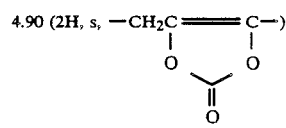

4.90 (2H, s, —CH$_2$C═══C—)

6.40–7.45 (8H,m,—NH and benzene ring).

What is claimed is:

1. (5-methyl-2-oxo-1,3-dioxolen-4-yl)methyl 2-(2,6-dichloroanilino)phenylacetate of the formula:

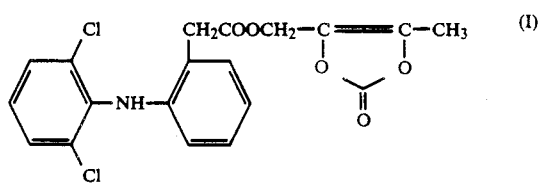

2. An anti-inflammatory composition, which comprises: (a) as an essential active ingredient a pharmaceutically effective amount of the compound according to claim 1, and (b) a pharmaceutical inert carrier therefor.

* * * * *